United States Patent
Gindele et al.

(10) Patent No.: US 11,047,842 B2
(45) Date of Patent: Jun. 29, 2021

(54) REMOTE WIRELESS SENSING APPARATUS

(71) Applicant: Rosemount Inc., Shakopee, MN (US)

(72) Inventors: Greg E. Gindele, Maple Lake, MN (US); Sean P. McLeskey, Eden Prairie, MN (US); Robert M. Weinberger, Prior Lake, MN (US)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 16/369,189

(22) Filed: Mar. 29, 2019

(65) Prior Publication Data

US 2020/0309755 A1    Oct. 1, 2020

(51) Int. Cl.
*G01N 33/00* (2006.01)
*H04Q 9/00* (2006.01)

(52) U.S. Cl.
CPC ....... *G01N 33/0062* (2013.01); *G01N 33/004* (2013.01); *G01N 33/0006* (2013.01); *H04Q 9/00* (2013.01); *H04Q 2209/40* (2013.01)

(58) Field of Classification Search
None
See application file for complete search history.

(56) References Cited

U.S. PATENT DOCUMENTS

| | | | |
|---|---|---|---|
| 7,633,963 B1 | 12/2009 | Anderson et al. | |
| 8,578,783 B2 | 11/2013 | Hedtke et al. | |
| 10,492,684 B2 * | 12/2019 | Khachaturian | ....... G06F 1/1632 |
| 2013/0319987 A1 | 12/2013 | Beistle et al. | |
| 2016/0119065 A1 * | 4/2016 | Tobias | ............ H04B 13/02 348/81 |
| 2020/0153225 A1 * | 5/2020 | Kralik | .......... H02H 11/006 |

FOREIGN PATENT DOCUMENTS

| | | |
|---|---|---|
| CN | 203644199 U | 6/2014 |
| CN | 200092067 U | 4/2017 |
| WO | 2017205723 A1 | 11/2017 |
| WO | 2018164354 A | 8/2018 |

OTHER PUBLICATIONS

International Search Report and Written Opinion for International Patent Application No. PCT/US2020/022921, dated Jul. 8, 2020, 10 pages.

First Chinese Office Aciion dated Apr. 1, 2021, for Chinese Patent Application No. 2020101957.3, 23 pages including English translation.

* cited by examiner

*Primary Examiner* — Adolf Dsouza
(74) *Attorney, Agent, or Firm* — Christopher R. Christenson; Kelly, Holt & Christenson PLLC

(57) ABSTRACT

A sensor module assembly includes a sensor housing that houses a sensing element configured to sense a characteristic of a process and generate a sensor signal indicative of the characteristic. The sensor module assembly includes a wireless device housing that houses communication circuitry configured to receive the sensor signal and a wireless transmitter configured to send the sensor signal wirelessly to a remote device. The sensor module assembly also includes a communication cable that communicatively couples the sensing element in the sensor housing to the communication circuitry in the wireless device housing.

13 Claims, 4 Drawing Sheets

REMOTE WIRELESS SENSING APPARATUS

BACKGROUND

The process industry often employs gas sensors in order to detect the presence of a particular gas, often as part of a safety system. This is important as many gases may be harmful to human health and/or the environment. Industrial gas sensors are normally mounted near the process area of a plant or control room, or an area to be protected. Generally, industrial gas sensors are installed at fixed locations and a cable connects the gas sensors to a monitoring system.

The discussion above is merely provided for general background information and is not intended to be used as an aid in determining the scope of the claimed subject matter.

SUMMARY

A sensor module assembly includes a sensor housing that houses a sensing element configured to sense a characteristic of a fluid and generate a sensor signal indicative of the characteristic. The sensor module assembly includes a wireless device housing that houses communication circuitry configured to receive the sensor signal and a wireless transmitter configured to send the sensor signal wirelessly to a remote device. The sensor module assembly also includes a communication cable that communicatively couples the sensing element in the sensor housing to the communication circuitry in the wireless device housing.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Gas sensors may be used to detect combustible, flammable and toxic gases. Gas sensors may include infrared point sensors, ultrasonic sensors, electrochemical gas sensors, and semiconductor sensors.

Figure 1:
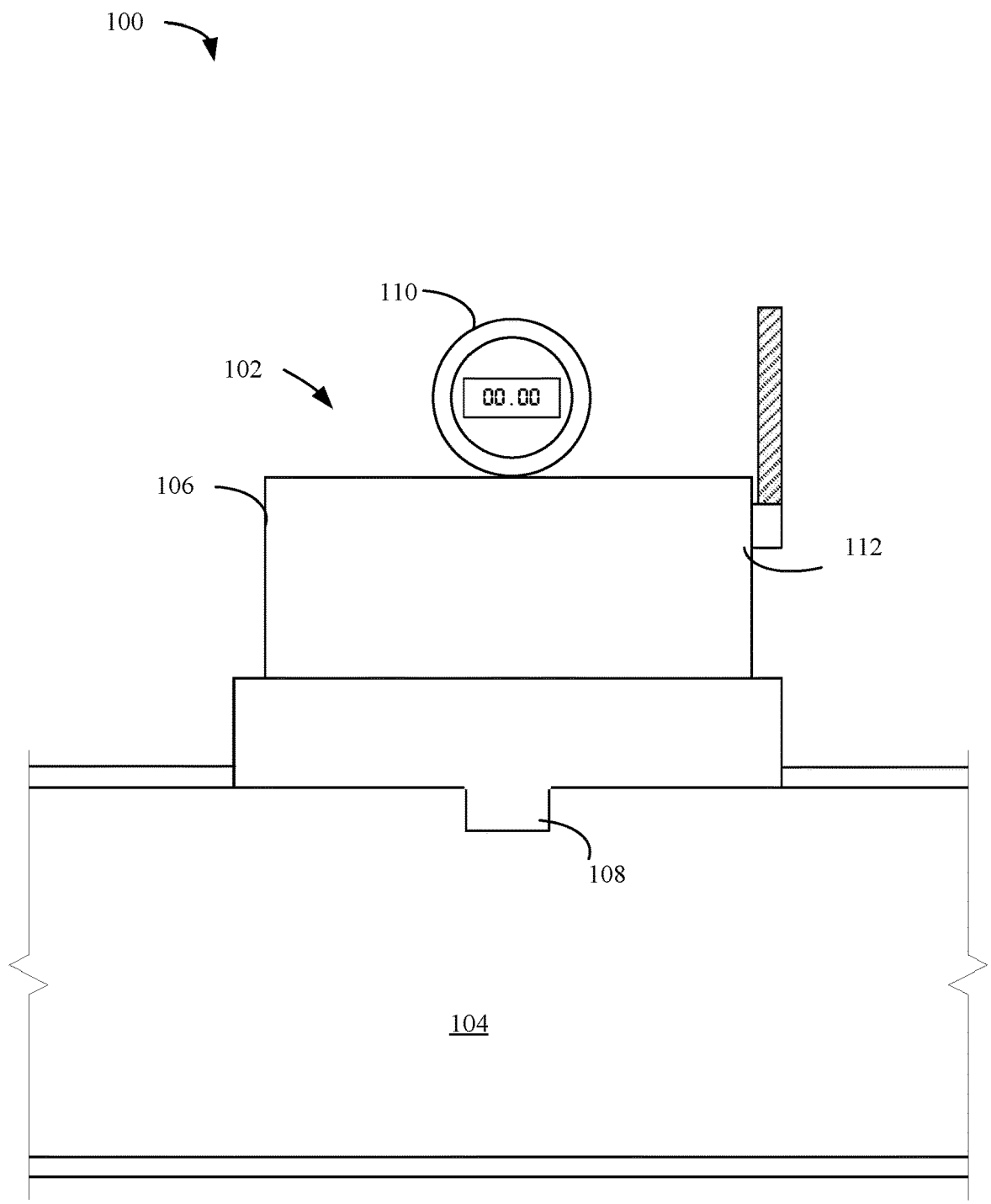
FIG. 1 is a diagram showing one example wireless sensor assembly.

FIG. 1 is a diagram showing an example sensor system. Sensor system 100, as shown, includes a sensor module 102 that senses a characteristic of process 104. To sense the characteristic, sensor module 102 has a sensing element 108 that is in contact with process 104. For example, sensing element may be a gas sensor and process 104 can comprise one or more gases. For instance, sensing element 108 can be a carbon dioxide detector and process 104 includes a bioreaction sensitive to carbon dioxide.

Sensor module 102 includes a housing 106 where circuitry coupled to the sensing element 108 is housed and protected. Housing 106 also houses communication circuitry coupled to wireless components 112 that allow for wireless communication of the sensed characteristics to be transmitted to another remote device.

Sensor module 102 also includes a user interface 110. User interface 110 can include a display showing the current value indicative of the characteristic being sensed by sensing element 108. For example, a value indicating the concentration of carbon monoxide in process 104 in parts per million (PPM) or a value indicating the concentration of oxygen in process 104 as a percentage. User interface 110 can also have user actuatable mechanisms that allow for control of sensor module 102. For example, mechanisms that facilitate establishing wireless connections between sensor module 102 and a remote device.

While it may be convenient to have wireless components within housing 106 of sensor module, it can be problematic to establish the wireless connection when sensor module 102 (and, hence user interface 110) is in a confined or inaccessible space. Additionally, having wireless components 112 on each sensor module 102 in a process environment can be costly and can increase the complexity of managing the process environment.

Figure 2:
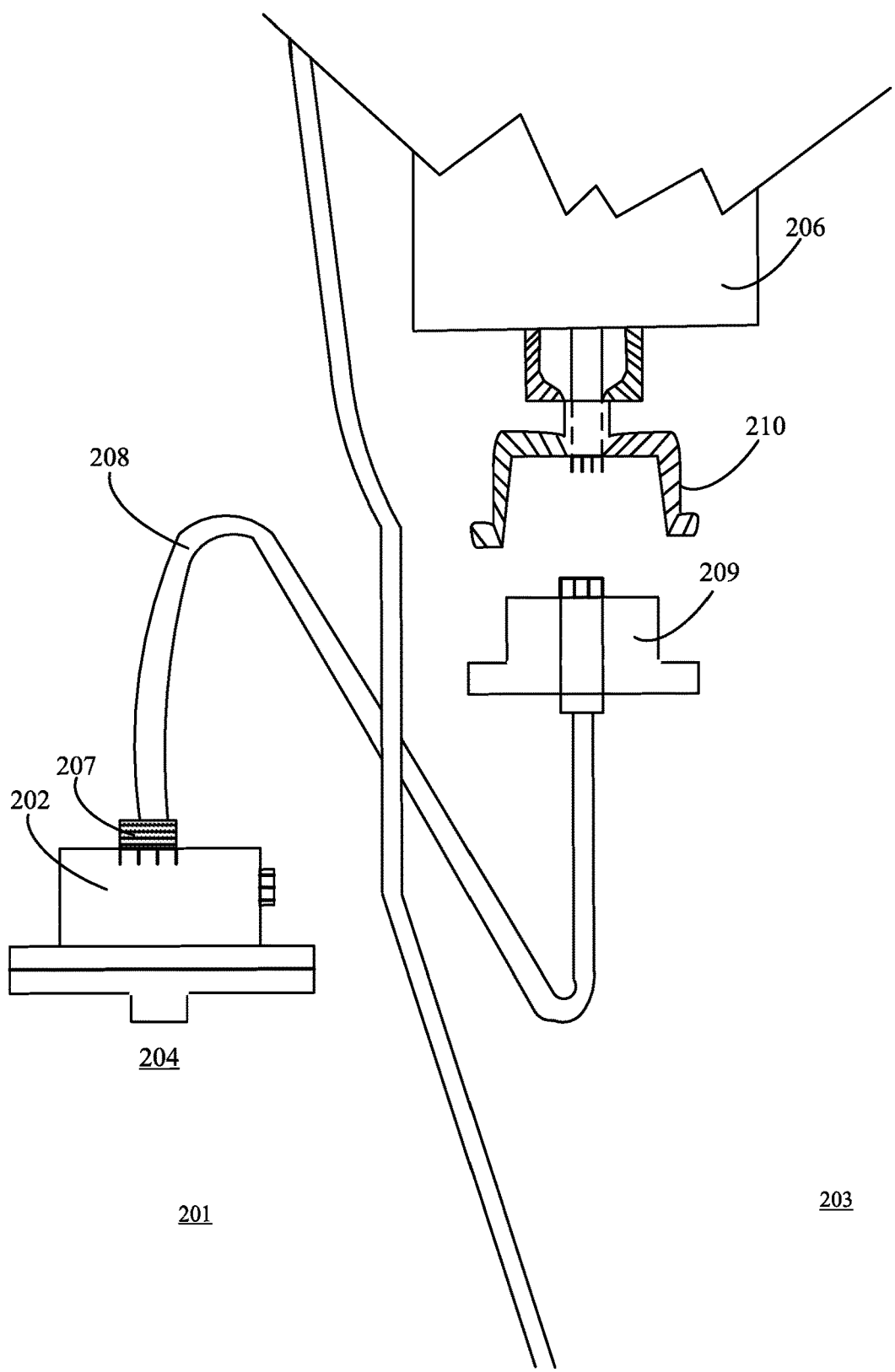
FIG. 2 is a diagram showing one example sensor and wireless device assembly.

FIG. 2 is a diagram showing one example of a remote sensor and wireless device assembly. As shown, remote sensor 202 is in an inaccessible area 201 and senses a characteristic of process 204. Illustratively, remote sensor 202 does not include wireless components that allow long-range communication of data sensed by a sensing element within remote sensor 202. Instead, remote sensor 202 is connected to a wireless device 206 that can wirelessly transmit data from remote sensor 202 to a remote device (e.g., a process control station, data analytics center, etc.). Remote sensor 202 conveys data to wireless device 206 through a wired connection (e.g., cable 208).

Cable 208 has a first interface 207 that allows a connection to remote sensor 202 and a second interface 209 that allows a connection to wireless device 206. Interface 207 and interface 209 can include permanent connections (e.g., solder, crimps, etc.) and/or can include removable connections (e.g., male/female connections, contact connections, etc.).

Interface 209 can couple indirectly to wireless device 206 via cable interface 210. Cable interface 210, as shown, includes an interface bus including pins and locking mechanisms that allow for removable coupling to wireless device 206. In other examples, cable interface 210 can couple to wireless device 206 in other ways, as well. Cable interface 210 can also allow for multiple cables to connect to wireless device 206, as shown in FIG. 3.

As shown, remote sensor 202 is in an inaccessible area 201 and wireless device 206 is in accessible area 203. An accessible area includes areas where a user can enter or access with relative ease. For example, an accessible area may allow a user to enter without donning any hazardous material protective equipment (e.g., respirator, HAZMAT suit, radiation protective equipment, etc.). As another example, an area may be inaccessible even if it does not require protective gear, if the area is hard to physically access, such as behind other equipment, high above or far below a working area, in a tight space, etc. Accordingly, if the sensor 202 is in an inaccessible area 201, it may be beneficial to have its user interface, such as an interface to control wireless connections, in an accessible area 203. For example, wireless device 206 can include a user interface, similar to user interface 110 in FIG. 1.

Figure 3:
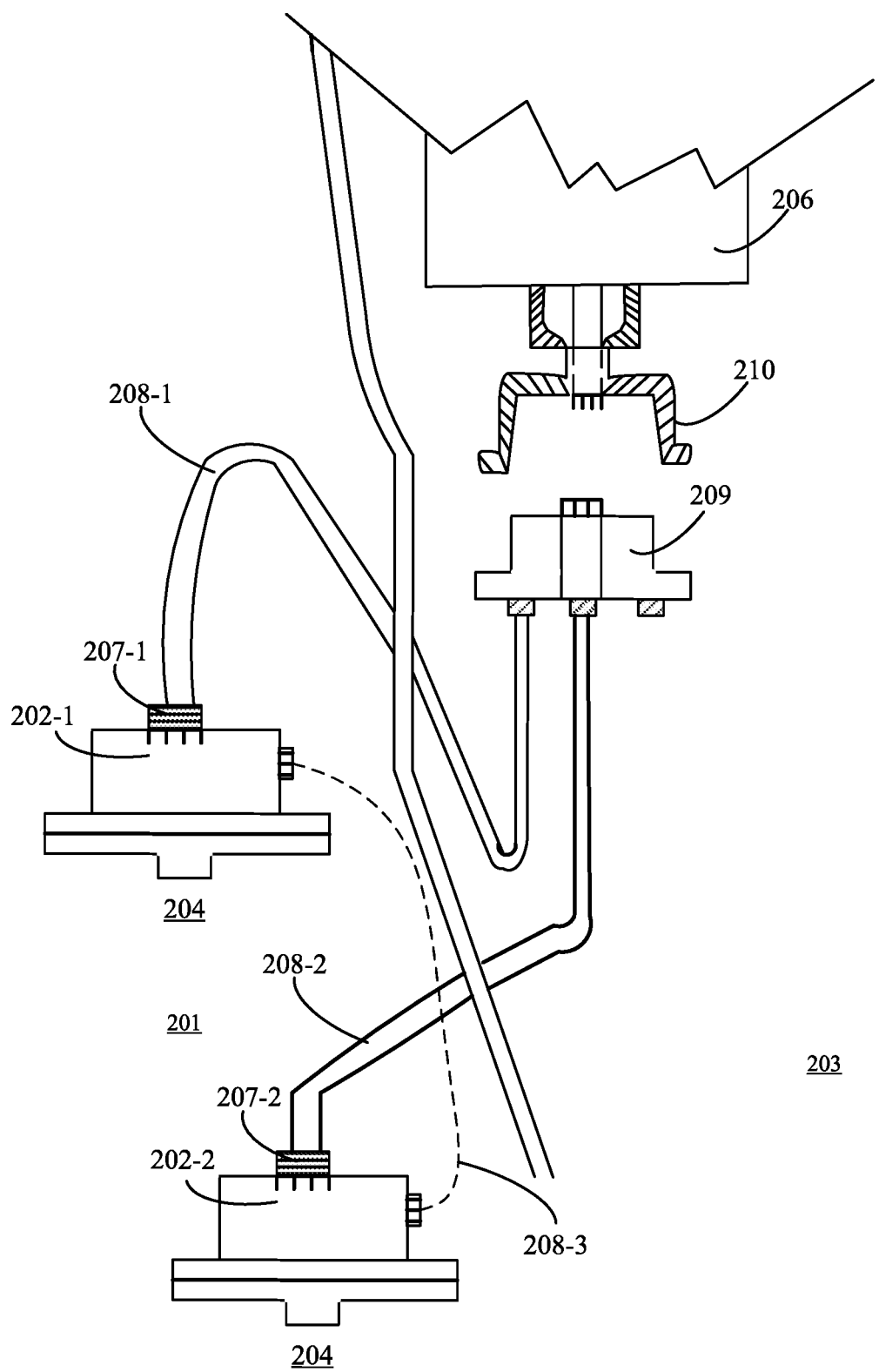
FIG. 3 is a diagram showing an example multiple sensor and wireless device assembly.

FIG. 3 is a diagram showing more than one sensor coupled to a wireless device. As shown, sensor 202-1 is coupled to wireless device 206 via cable 208-1 and sensor 202-2 is coupled to wireless device 206 via cable 208-2. Both cable 208-1 and cable 208-2 are coupled to wireless device 206 via a direct connection to interface 209. In other examples, there may be only one of cable 208-1 or cable 208-2 directly connected to interface 209, and instead remote sensor 202-1 and remote sensor 202-2 are connected to one another via cable 208-3 and their sensed data is then transmitted to wireless device 206 via either cable 208-1 or cable 208-2. This way, the sensors are chained together and only one cable is connected to wireless device 206 and transmits data from both sensors 202-1 and 202-2. In other examples, there may be a wireless device 206 for each sensor 202.

Figure 4:
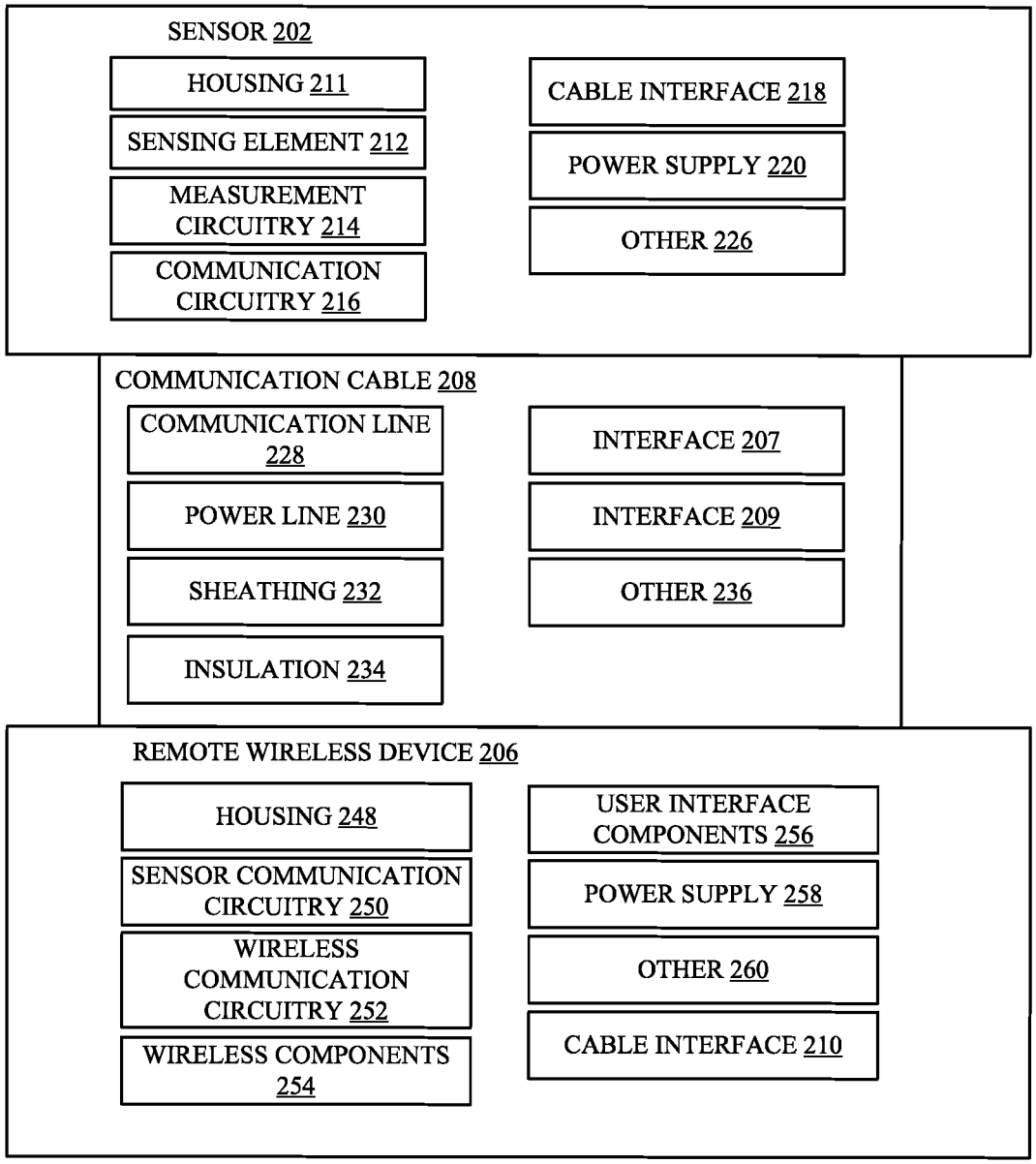
FIG. 4 is a block diagram showing one example sensor and wireless device assembly.

FIG. 4 is a block diagram showing an example sensor and remote wireless device assembly. Illustratively, sensor 202 is coupled to and, is in communication with, wireless device 206 via cable 208. Sensor 202 includes housing 211 which houses or otherwise couples a variety of different components that provide the functionality of sensor 202.

Sensor 202 includes sensing element 212 that is in direct or indirect contact with an object or environment and senses a characteristic of that object/environment. Sensing element 212 generates a sensor signal indicative of the characteristic that it is sensing. For example, sensing element 212 can sense a characteristic of process 204 and output a voltage that varies with the characteristic. Measurement circuitry 214 is communicatively coupled to sensing element 212 to condition or otherwise processes the sensor signal generated by sensing element 212. For example, measurement circuitry 214 can include amplifiers, analog-to-digital converters, filters, etc. For instance, assume a sensor 202 outputs a given analog voltage, in this instance measurement circuitry 214 could include an analog-to-digital converter and some processing logic to translate the voltage into a metric (e.g., an oxygen concentration in percentage).

Sensor 202 also includes communication circuitry 216 that is communicatively coupled to measurement circuitry 214 and cable interface 218. Communication circuitry 216 can transmit data from measurement circuitry 214 to other components (e.g., wireless device 206). Prior to transmission communication circuitry 216 can further process the data, for example, arranging the data in a more suitable form for transmission (e.g., encoding, etc.). Communication circuitry 216, as shown, transmits data to other components through cable 208 via cable interface 218.

Cable interface 218 can include permanent connections (e.g., solder, crimps, etc.) and/or can include removable connections (e.g., male/female connections, contact connections, etc.) to interface 207 of cable 208. Cable interface 218 can also include connections to allow chaining of sensors 202 together, such as cable 208-3 in FIG. 3.

The above-mentioned components of sensor 202 can be powered by a power supply 220. In some examples, sensor 202 can be powered in addition to, or alternatively by an external power supply. Of course, these components are examples only and sensor 202 can include other items as well, as indicated by block 226.

Communication cable 208 illustratively includes interface 207 that couples to sensor 202 and interface 209 that couples to wireless device 206. Interface 207 and/or interface 209 can include permanent connections (e.g., solder, crimps, etc.) and/or can include removable connections (e.g., male/female connections, contact connections, etc.) to facilitate connections to their respective components. In some examples, sensor 202 has an interface 209 can directly connect to cable interface 210 without the use of a cable 208.

Communication cable 208 facilitates data transfers between sensor 202 and wireless device 206 via communication line 228. Communication line 228 can include a variety of different data conduits. For example, communication line 228 can include electrically conductive materials (e.g., copper, silver, gold, etc.), fiber optics, etc. In some examples, communication cable 208 can also supply power to either sensor 202 or wireless device 206 via powerline 230.

Communication cable 208 can include sheathing 232 that provides protection from physical contact, chemical, Ultraviolet resistance, or other wear or damage. Communication cable 208 also include insulation 234 that protects communication line 228 and powerline 230 from external influences (e.g., electric/magnetic/radioactive interference, noise, etc.) Communication cable 208 can include other items as well, as indicated by block 236.

Wireless device 206 includes a housing 248 that houses or otherwise couples to components of wireless device 206. As noted above, wireless device 206 transmits data wirelessly that it receives from sensor 202 via cable 208. Cable 208 physically couples to wireless device 206 via cable interface 210. Cable interface 210 can include permanent connections (e.g., solder, crimps, etc.) and/or can include removable connections (e.g., male/female connections, contact connections, etc.) that allow coupling of cable 208 to wireless device 206. In some examples, cable 208 can be coupled to wireless device 206 tool-lessly.

Wireless device 206 includes sensor communication circuitry 250 that receives, and processes signals received through cable interface 210. Wireless device 206 can then transmit this data wirelessly to a remote device. Suitable examples of some process industry wireless communication protocols include the Highway Addressable Remote Transducer (HART®) protocol, the FOUNDATION™ Fieldbus protocol, or wireless process communication protocols, such as IEC 62591 (2.4 GHz ISM band). To facilitate this wireless transfer wireless communication circuitry 252 processes a signal for wireless transfer to a remote location via wireless components 254. Wireless components 254 can include antennas and other broadcasting components. Sensor communication circuitry 250 can also send data or commands to sensor 202. For example, a user may actuate user interface components 256 of wireless device 206 to control the operation of sensor 202 (e.g., establishing a connection, running a calibration, controlling sensor sensitivity, etc.)

A user can interact with wireless device 206 via user interface components 256 to initialize a wireless connection between wireless device 206 (and by extension sensor 202) and another remote device. User interface components 256 can include displays, electrical buttons, etc. that can also facilitate control of other functionalities of wireless device 206 and any sensor 202 coupled to wireless device 206 via cables 208.

The above-mentioned components of wireless device 206 can be powered by a power supply 258. In some examples, wireless device 206 can be powered in addition to, or alternatively by an external power supply or powerline 230. Of course, the above-mentioned components are examples only and wireless device 206 can include other items as well, as indicated by block 260.

Although the present invention has been described with reference to preferred embodiments, workers skilled in the art will recognize that changes may be made in form and detail without departing from the spirit and scope of the invention.

What is claimed is:

1. A wireless sensor module assembly comprising:
   a gas sensor comprising:
      a sensor housing mountable within an area to protect;
      a gas sensing element disposed in the sensor housing configured to sense a gas and generate a gas sensor signal indicative of the sensed gas;
   a wireless device comprising:
      a wireless device housing mountable in a user accessible location, the wireless device housing being spaced from the sensor housing;
      communication circuitry configured to receive the gas sensor signal; and
      a wireless transmitter disposed within the wireless device housing and configured to transmit wireless information to a remote device based on the gas sensor signal in accordance with a wireless process industry standard protocol; and
   a communication cable that physically and communicatively couples the gas sensing element to the communication circuitry of the wireless device.

2. The wireless sensor module assembly of claim 1, wherein the communication cable comprises sheathing and insulation.

3. The wireless sensor module assembly of claim 1, wherein the communication cable comprises a powerline configured to supply power to the sensor or wireless device.

4. The wireless sensor module assembly of claim 1, further comprising a second gas sensor comprising:
   a second gas sensing element that is coupled to the communication circuitry by a second communication cable.

5. The wireless sensor module assembly of claim 1, wherein the wireless device comprises a user interlace mechanism.

6. The wireless sensor module assembly of claim 5, wherein the user interface mechanism comprises a display that displays a current value sensed by the sensor.

7. The wireless sensor module assembly of claim 5, wherein the user interface mechanism comprises a user actuatable mechanism that, when actuated, calibrates the gas sensor.

8. The wireless sensor module assembly of claim 1, wherein the wireless device comprises a cable interface that receives and removably couples to the communication cable.

9. The wireless sensor module assembly of claim 8, wherein the cable interface is a tool-less interface.

10. The wireless sensor module: assembly of claim 1, wherein the gas sensor is disposed in an inaccessible area of a process environment and the wireless device is disposed in an accessible area of the process environment.

11. The wireless sensor module assembly of claim 1, wherein the wireless transmitter transmits data over a 2.4 GHz ISM band.

12. The wireless sensor module assembly of claim 1, wherein the communication cable is:
   a shielded communication cable that couples the gas sensing element to the wireless transmitter, such that the gas sensor signal is received by the wireless transmitter; and
   wherein the shielded communication cable comprises a first end that couples to the gas sensing element and a second end that removably couples to a bus of the wireless device housing.

13. The wireless sensor module assembly of claim 12, wherein the bus of the wireless device housing comprises a plurality of ports, each port configured to receive one of a plurality of shielded communication cables that communicatively couple to a plurality of gas sensors.

* * * * *